US00PP25902P2

(12) United States Plant Patent
Ault

(10) Patent No.: US PP25,902 P2
(45) Date of Patent: Sep. 15, 2015

(54) ***BAPTISIA* PLANT NAMED 'BLUE MOUND'**

(50) Latin Name: *Baptisia australis*
Varietal Denomination: Blue Mound

(71) Applicant: James R. Ault, Libertyville, IL (US)

(72) Inventor: James R. Ault, Libertyville, IL (US)

(73) Assignee: CHICAGO LAND GROWS, INC., Glencoe, IL (US)

( * ) Notice: Subject to any disclaimer, the term of this patent is extended or adjusted under 35 U.S.C. 154(b) by 119 days.

(21) Appl. No.: 13/998,942

(22) Filed: Dec. 24, 2013

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Penny J. Aguirre

(57) ABSTRACT

A new cultivar of *Baptisia australis*, 'Blue Mound', that is characterized by its dense, uniform, rounded, and low growing plant habit, its foliage that completely masks the bases of the main stems, its inflorescences that are held above the foliage, its 1.9 cm wide flowers that are deep violet in color and bloom from mid May to early June in northern Illinois, its high level of fertility; setting a good quantity of fruit with viable seed, its green stems that do not lodge after summer rainstorms, and its tolerance of both acidic and alkaline soil.

2 Drawing Sheets

Botanical classification: *Baptisia australis*.
Cultivar designation: 'Blue Mound'.

BACKGROUND OF THE INVENTION

The present invention relates to a new and distinct cultivar of hybrid *Baptisia* plant, botanically known as *Baptisia australis* 'Blue Mound' and will be referred to hereafter by its cultivar name, 'Blue Mound'. The new cultivar represents a new herbaceous perennial grown for landscape use.

The new invention arose from an ongoing breeding program conducted by the Inventor in Glencoe, Ill. 'Blue Mound' was derived from a cross made in May of 1999 between an unnamed plant of *Baptisia australis* var. *minor*, as the female parent, and an unnamed plant of *Baptisia australis* var. *australis*, as the male parent. The resulting seedlings were planted for evaluation in spring of 2000. 'Blue Mound' was selected in October of 2008 as a single unique plant amongst the resulting seedlings.

Asexual propagation of the new cultivar was first accomplished by rooting of shoot tip cuttings in July of 2009 in Glencoe, Ill. under the direction of the Inventor. Asexual propagation by stem shoot tip cuttings has determined that the characteristics of the new cultivar are stable and are reproduced true to type in successive generations.

SUMMARY OF THE INVENTION

The following traits have been repeatedly observed and represent the characteristics of the new cultivar as observed in Glencoe, Ill. These attributes in combination distinguish 'Blue Mound' as a unique cultivar of *Baptisia*.

1. 'Blue Mound' exhibits a dense, uniform, rounded, and low growing plant habit.
2. 'Blue Mound' exhibits foliage that completely masks the bases of the main stems.
3. 'Blue Mound' exhibits inflorescences that are held above the foliage.

4. 'Blue Mound' exhibits 1.9 cm wide flowers that are deep violet in color and bloom from mid May to early June in northern Illinois.
5. 'Blue Mound' exhibits a high level of fertility; setting a good quantity of fruit with viable seed.
6. 'Blue Mound' exhibits green stems that do not lodge after summer rainstorms.
7. 'Blue Mound' exhibits tolerance of both acidic and alkaline soil.

The female parent of 'Blue Mound', an unnamed plant of *Baptisia australis* var. *minor*, differs from 'Blue Mound' in being shorter in height and narrower in width, in being less flower bud hardy in U.S.D.A. Zone 5, and in producing fewer flowers per inflorescence. The male parent of 'Blue Mound', an unnamed plant of *Baptisia australis* var. *australis*, differs from 'Blue Mound' in having a more upright, irregular plant habit, in being taller in height, and in having stems that lodge after summer rainstorms. 'Blue Mound' can be most closely compared to the *Baptisia* cultivars 'Royal Purple' (U.S. Plant Pat. No. 25,508) and 'Purple Smoke' (not patented). 'Royal Purple' is similar to 'Blue Mound' in having flowers that are dark violet in color and in growing wider than taller over time. 'Royal Purple' differs from 'Blue Mound' in having an vase-shaped plant habit with a broad, rounded, irregular shaped head of foliage borne above the main stems, in having stem bases that are visible below the foliage, in having fewer flowers per inflorescence, and in having flowers that are larger in width. 'Purple Smoke' is similar to 'Blue Mound' in having flowers that are violet in color, in having a three-week long blooming period beginning in mid-May in northern Illinois, and in having a bushy rounded plant habit. 'Purple Smoke' differs from 'Blue Mound' in having stems that are gray in color, in being taller in height and not as wide growing, in rarely, if ever, producing viable seed, and in having visible stem bases beneath the main foliar mass.

BRIEF DESCRIPTION OF THE DRAWINGS

The accompanying colored photographs illustrate the overall appearance and distinct characteristics of the new *Bapti-*

*sia*. The photographs were taken of plants ten years in age as grown outdoors in a trial plot in Glencoe, Ill.

Figure 1:
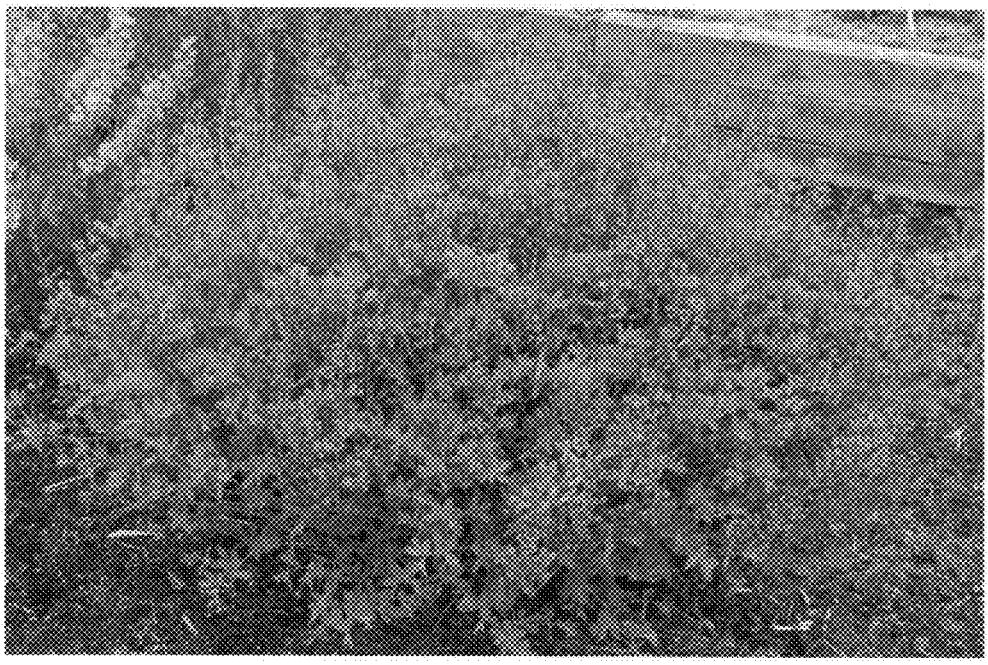

The photograph in FIG. 1 is a side view of 'Blue Mound' in bloom and illustrates the plant habit and flowering habit.

Figure 2:
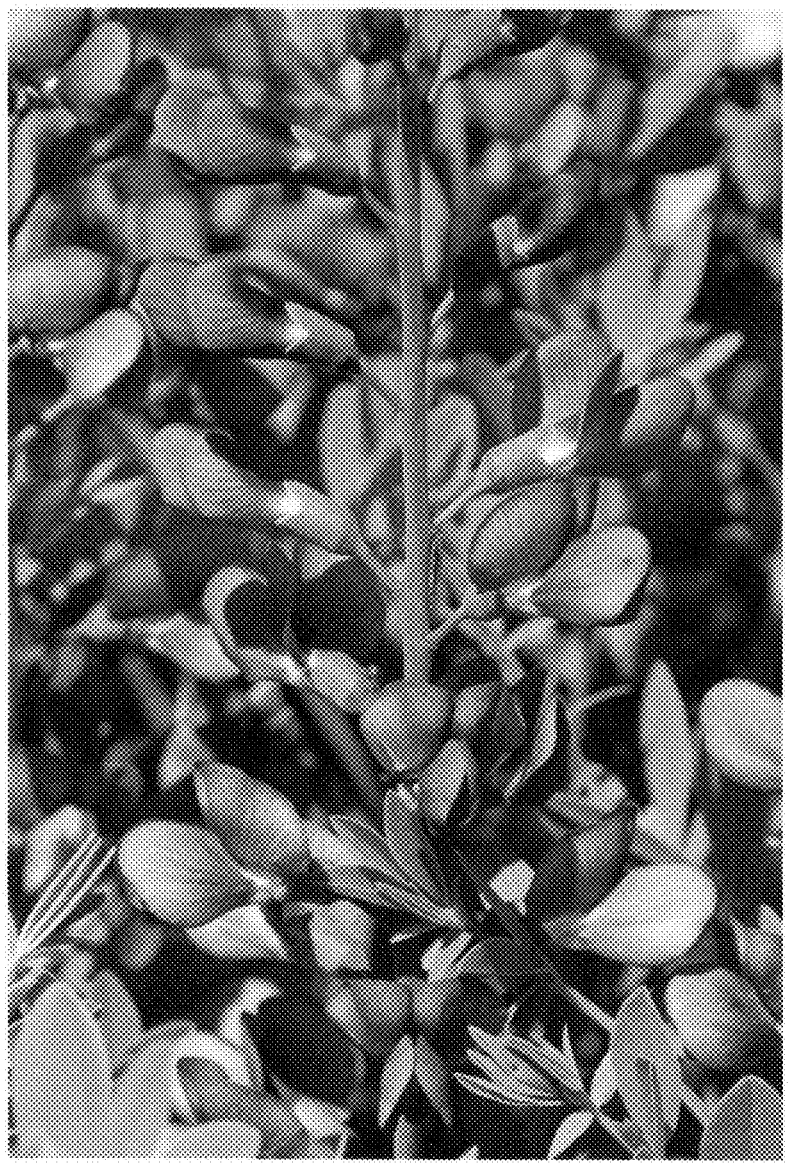

The photograph in FIG. 2 provides a close up view of the flowers of 'Blue Mound'.

The colors in the photographs are as close as possible with the photographic and printing technology utilized and the color values cited in the detailed botanical description accurately describe the colors of the new *Baptisia*.

DETAILED BOTANICAL DESCRIPTION OF THE PLANT

The following is a detailed description of ten year-old plants of the new cultivar as grown outdoors in a trial plot in Glencoe, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Three weeks from mid May to early June in northern Illinois.

*Plant type.*—Herbaceous perennial.

*Plant habit.*—Dense, uniform, rounded, and low growing plant habit with flower racemes held above the foliage and foliage that completely masks the bases of the main stems.

*Height and spread.*—Reaches an average of 109 cm in height and 152 cm in width after ten years of growth.

*Hardiness.*—U.S.D.A. Zones 4 to 8.

*Diseases and pests.*—No susceptibility to diseases or pests has been observed.

*Root description.*—Fine and fibrous.

*Propagation.*—Rooting of shoot tip cuttings.

*Growth rate.*—Vigorous.

Stem description:

*Branch habit.*—Densely branched; average of 117 main branches with an average of 4 secondary branches, and 2 tertiary branches.

*Stem size.*—Main stem; an average of 48 cm (including peduncle) in length and 5 mm in width, secondary; average of 30 cm in length and 5 mm, tertiary; an average of 5.5 cm in length and 2 mm in width.

*Stem shape.*—Oval.

*Stem color.*—144A.

*Stem surface.*—Hairless, satiny but slightly glaucous.

Foliage description:

*Leaf shape.*—Fan-shaped in overall outline.

*Leaf division.*—3-palmate.

*Leaf internode.*—Foliage begins near the base of the main stems, an average of 7 cm on main stem and an average of 5.5 cm on secondary branches.

*Leaf size.*—About 3 cm in length and 1 cm in width.

*Leaf quantity.*—About 30 per stem.

*Leaflet shape.*—Oblanceolate.

*Leaflet base.*—Cuneate.

*Leaflet apex.*—Acute.

*Leaflet venation.*—Pinnate pattern, not conspicuous, color matches leaflet color on the upper and lower surface with the mid rib on lower surface N137D.

*Leaflet margins.*—Entire.

*Leaf attachment.*—Petiolate.

*Leaf arrangement.*—Alternate.

*Leaflet surface.*—Glabrous and slightly glaucous on upper and lower surface.

*Leaflet color.*—Newly expanded and mature; upper and lower surface N137D.

*Leaflet size.*—An average of 1 cm in length and 2 mm in width.

*Petioles.*—Average of 5 mm in length and 1 mm in width, clasping to stem at mature nodes, N144A in color, surface is glabrous and satiny.

*Stipules.*—On basal 2 to 3 nodes prior to leaves; single, ovate in shape, about 6 mm in length and 2 mm in width, truncate base, acute apex, 137A in color.

Flower description:

*Inflorescence type.*—Terminal racemes of pea-like flowers on main and secondary branches, blooms from the base to the apex.

*Inflorescence size.*—Average of 12 cm in length and 4.5 cm in width in mid section.

*Lastingness of inflorescence.*—3 to 4 weeks.

*Flower size.*—About 2 cm in depth and about 1.5 cm in diameter.

*Flower fragrance.*—Faint.

*Flower number per inflorescence.*—Average of 40.

*Peduncle.*—Round in shape, up to 23 cm in length and an average of 5 mm in width, 144B in color, surface is glabrous, satiny and slightly glaucous, flower internode length averages from whorls to about 5 mm.

*Pedicel.*—About 5 mm cm in length, about 1 mm in width, oval in shape, N144C, glabrous and satiny surface.

*Flower buds.*—Kidney-shaped, about 1.5 cm in length and 0.7 cm in width, color of petal portion is a blend of N88A and a sliver of exposed keel portion 196A, calyx portion same as open flowers.

*Flower type.*—Papilionaceous, held at about a 45° angle.

*Calyx.*—Campanulate, about 1 cm in length and 5 mm in diameter, surface is glabrous and satiny, 144C in color, persistent.

*Sepals.*—5, fused with the exception of apex of each, free portion is triangular in shape 2 mm in width and 2 mm in depth with an acute apex, 144C.

*Corolla features.*—Papilionaceous (4 segments) with a keel, a banner and 2 lateral wings, lateral wings; obelliptic in shape, about 1.5 cm in length and 9 mm in width, color on outer surface and the inner surface is N88A, rounded apex, oblique base, keel; only partially visible, comprised of 2 segments surrounding reproductive organs, oblong (slightly oblique) in shape with rounded apex and oblique base, 1.5 cm in length and 1 cm in width, upper surface and lower surface are a blend of N88A and N88B in color, banner; orbicular in shape, about 2 cm in length and 1 cm in width, upper and lower surface is 90A with the basal portion 150D and mid section marked with 146B, apex is rounded with a single notch, surface is glabrous on all sections.

*Receptacle.*—Disk-shaped, gelatinous, 137A in color, 3 mm in diameter and 1.2 mm in depth.

Reproductive organs:

*Gynoecium.*—1 Pistil, about 1.5 cm in length, 2 mm in width; style is 145A in color and 5 mm in length; stigma minute, too small to read color, ovary is superior, 146A in color, 5 mm in length and 1 mm in width.

*Androcoecium.*—10 stamens, not united, 1.5 cm in length and 1 mm in width; filament is 1.4 cm in length, 1 mm in width and 145A in color; anther is dorsifixed, 2 mm in length and width and 168B in color, pollen is abundant and 161A in color.

*Fruit.*—An inflated pod, technically a legume, average of 3 produced per inflorescence (open-pollinated), elliptic-oblong in shape, average of 4 cm in length by 1.6 cm in width with a beak approx. 1 cm in length, color of outer and inner surface when mature is a blend of 200A and 200C, walls 1.5 mm and hard at maturity, seed; average of 9 per fruit (open-pollinated), 200A in color, oval with the hilum side more or less straight, seed compressed to flattish, 4 mm in length, 3 mm in width and 2 mm in thickness.

It is claimed:

1. A new and distinct cultivar of *Baptisia* plant named 'Blue Mound' as herein illustrated and described.

* * * * *